(12) United States Patent
Taylor

(10) Patent No.: US 8,574,194 B2
(45) Date of Patent: Nov. 5, 2013

(54) INJECTION SITE MARKING METHOD

(76) Inventor: Robert C. Taylor, Nashville, TN (US)

(*) Notice: Subject to any disclaimer, the term of this patent is extended or adjusted under 35 U.S.C. 154(b) by 0 days.

(21) Appl. No.: 13/326,406

(22) Filed: Dec. 15, 2011

(65) Prior Publication Data

US 2013/0158481 A1    Jun. 20, 2013

(51) Int. Cl.
 *A61M 5/42* (2006.01)
(52) U.S. Cl.
 USPC ......................................................... 604/116
(58) Field of Classification Search
 USPC ...................................... 604/116; 606/1, 116
 See application file for complete search history.

(56) References Cited

U.S. PATENT DOCUMENTS

| | | | |
|---|---|---|---|
| 4,838,854 A * | 6/1989 | Kuzmanovich | 604/506 |
| 5,192,270 A | 3/1993 | Carswell, Jr. | |
| 6,322,536 B1 | 11/2001 | Rosengart et al. | |
| 6,436,105 B1 * | 8/2002 | Passmore | 606/116 |
| 7,100,646 B2 * | 9/2006 | Py et al. | 141/329 |
| 7,824,922 B2 * | 11/2010 | Kacian et al. | 436/180 |
| 2003/0040706 A1 * | 2/2003 | Kuracina et al. | 604/116 |
| 2007/0255175 A1 * | 11/2007 | Sangha | 600/572 |
| 2011/0137250 A1 | 6/2011 | Kraft | |
| 2012/0283637 A1 * | 11/2012 | Cohen | 604/116 |

* cited by examiner

*Primary Examiner* — Nicholas Lucchesi
*Assistant Examiner* — Benjamin Koo
(74) *Attorney, Agent, or Firm* — Dale J. Ream

(57) ABSTRACT

An injection site marking method and apparatus includes a base member having a continuous side wall defining an open top, an open bottom, and an interior area. The open bottom is configured to attach selectively to a serum vial. A liquid retention member is positioned in the interior area and configured to hold a colorized viscous liquid. A cap having a continuous side wall defining an open bottom and interior area is connected to the base member such that the liquid retention member is unexposed. The cap includes a top wall defining an aperture. In use, a syringe may be inserted through the aperture, through the liquid retention member, and into a serum vial so as to withdraw serum and such that the syringe reservoir nose contacts the viscous liquid. The needle is injected into a user's skin until the syringe reservoir nose contacts the skin with the colorant.

8 Claims, 3 Drawing Sheets

INJECTION SITE MARKING METHOD

BACKGROUND OF THE INVENTION

This invention relates generally to injection site marking devices and, more particularly, to an injection site marking method and apparatus.

Persons having certain illnesses, medical conditions, or diseases must inject themselves or be injected by another person using a syringe filled with a liquid medicament. For example, a person having diabetes may be required to inject himself with insulin every day. In fact, some diabetics must inject themselves with multiple types of insulin every day. It is not recommended to inject into the same skin location on consecutive days as this may result in the breakdown of skin tissue. In addition, it is difficult for a diabetic to keep track of which type of insulin has or has not been injected—resulting in the risk that the same type of insulin may be injected twice while another type of insulin may not be injected at all.

Various devices have been proposed for identifying the site of a syringe injection so as to aid a user in not injecting in the same site on consecutive days. Specifically, U.S. Pat. No. 5,192,270 discloses that a protective needle cover includes a dimple having a small amount of pigment therein such that the cover may be pressed against a user's skin before or after injection to identify an injection site. Although assembly effective, the existing patents do not provide for an injection site marking to be made simultaneous with the process of making an injection. Further, the past patents and proposals do not solve the problem of indicating from which of multiple vials have been injected at one sitting.

Therefore, it would be desirable to have a method and apparatus for marking an injection site that makes a marking on a user's skin simultaneous with making an injection. Further, it would be desirable to have a method and apparatus for marking an injection site that makes it easy for a user to determine which medicine from multiple vials has been injected and which has not been injected.

SUMMARY OF THE INVENTION

An injection site marking method and apparatus according to the present invention includes a base member having a continuous side wall defining an open top, an open bottom, and an interior area. The open bottom is configured to attach selectively to a serum vial. A liquid retention member is positioned in the interior area and configured be saturated by a viscous liquid such as saline and colorant. A cap having a continuous side wall defining an open bottom and interior area is connected to the base member such that the liquid retention member is unexposed. The cap includes a top wall defining an aperture. In use, a syringe may be inserted through the aperture, through the liquid retention member, and into a serum vial to withdraw serum and such that the syringe reservoir nose contacts the viscous liquid. The needle is then injected into a user's skin until the syringe reservoir nose contacts the skin and leaves a colorant marking.

Therefore, a general object of this invention is to provide an injection site marking method and apparatus for identifying on a user's skin the site at which a particular medicine was injected.

Another object of this invention is to provide an injection site marking method and apparatus, as aforesaid, that includes a marking apparatus that attaches selectively to a medicament vial and causes a syringe and needle to be marked with a color while medicine is drawn from the vial into the syringe reservoir.

Still another object of this invention is to provide an injection site marking method and apparatus, as aforesaid, in which the marking apparatus includes a sponge saturated with a viscous liquid such as an all natural colored solution.

Yet another object of this invention is to provide an injection site marking method and apparatus, as aforesaid, in which the marking apparatus includes one or more porous dividers that allow a syringe needle to pass therethrough while preventing leakage of the viscous liquid.

A further object of this invention is to provide an injection site marking method and apparatus, as aforesaid, that is easy, clean, and sanitary to use.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

Figure 1:
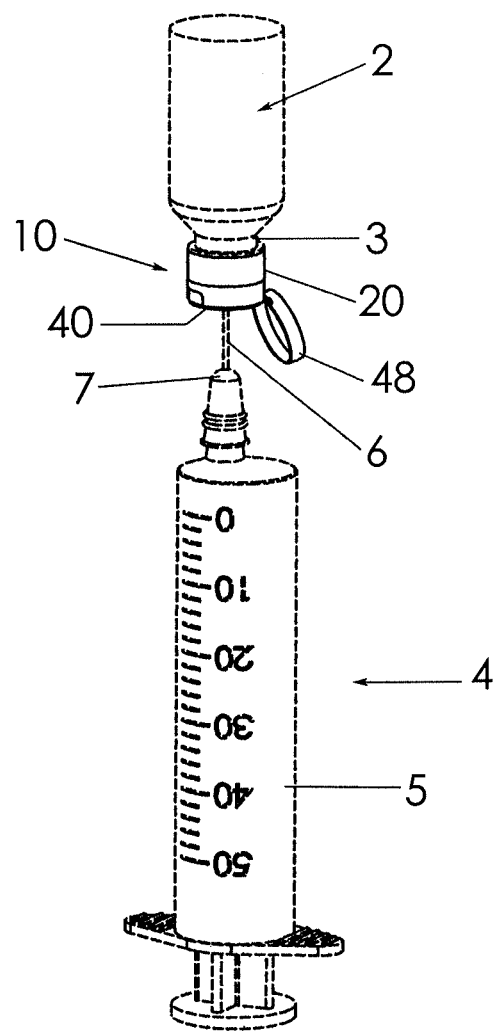
FIG. 1 is a perspective view of an injection site marking apparatus with a syringe according to a preferred embodiment of the present invention.

An injection site marking apparatus and method according to a preferred embodiment of the present invention will now be described with reference to FIGS. 1 to 3b of the accompanying drawings. The marking apparatus 10 includes a base member 20, liquid retention member 30, and a cap 40 as described below. It is understood that a medicine vial 2 (also referred to as a serum vial) includes a neck portion 3 and a seal at an upper end thereof although it is understood that a serum vial 2 itself and its contents are preferably not a part of the invention.

Figure 3A:
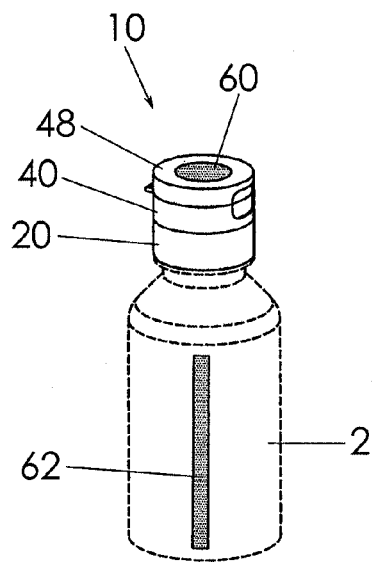
FIG. 3a is a perspective view of the marking apparatus as in FIG. 1 shown coupled to a medicine vial.

The base member 20 includes a continuous side wall 22 that defines an open top and substantially open bottom. In other words, the base member side wall 22 defines a bore therethrough that also defines an interior area. The base member open bottom 26 is configured to be coupled selectively to an upper end of a medicine vial neck portion 3 (FIG. 3a). In some embodiments, the base member 20 may include a bottom wall 27 defining the substantially open bottom, the open bottom having a diameter slightly larger than a diameter of the serum vial neck portion 3 so that the base member 20 may be coupled thereto in a friction fit arrangement. The base member interior area is configured to receive the liquid retention member 30.

The cap 40 includes a continuous side wall 42 that defines an open bottom 41 and a cap interior area. The cap 40 includes a top wall 44 that defines an aperture 46, the aperture 46 providing access to the cap interior area as will be further described later. The lower edge of the cap side wall 42 and the upper edge of the base member side wall 22 have complementary cylindrical configurations and are coupled together in a friction fit, snap fit, heat seal, plastic welding, or adhesive engagement such that the interior areas of the base member 20 and cap 40 are adjacent one another. In practice, the combined interior areas described above are configured to receive respective portions of the liquid retention member 30.

The liquid retention member 30 is configured to be saturated with a viscous liquid. The liquid retention member 30 may be constructed of a sponge or sponge-like material that is capable of being saturated with a thick viscous substance. Preferably, the viscous liquid is a saline solution with an all-natural colorant. This is important in that the saline solution may be coated onto the syringe needle and, therefore, be safely injected under a user's skin during use. In other embodiments, the viscous liquid may be ink or dye although formulations that are safe when injected under the skin are preferred.

Figure 2:
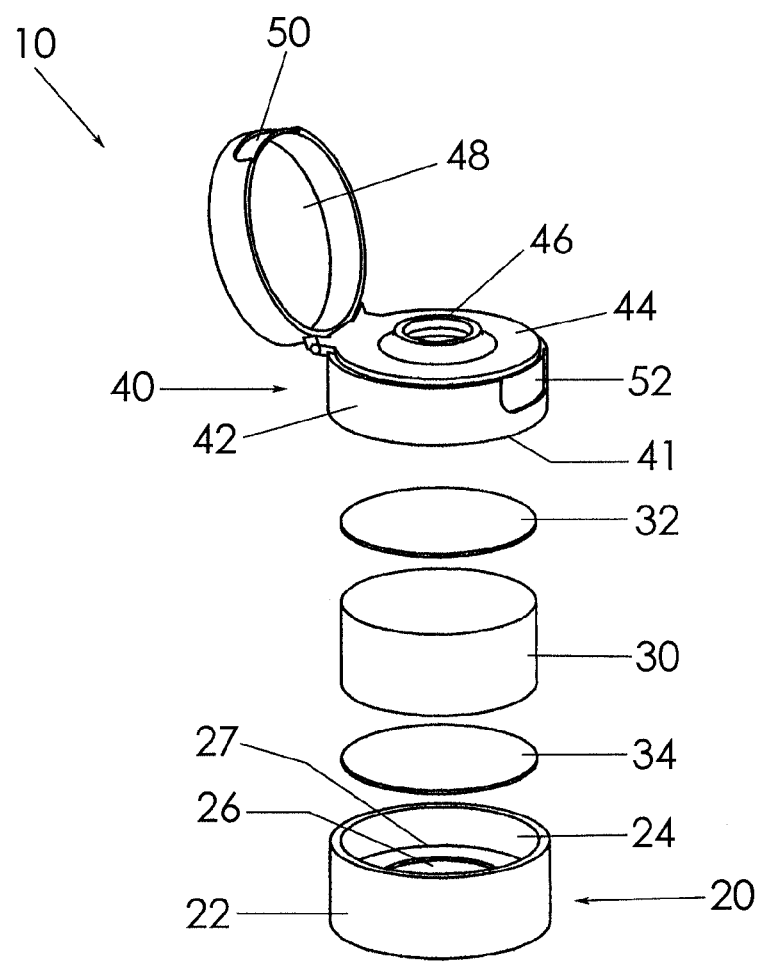
FIG. 2 is an exploded view of the marking apparatus as in FIG. 1.

A lid 48 may be pivotally coupled to the cap 40 that is selectively movable between a closed configuration preventing access to the cap aperture 46 and an open configuration providing access to the cap aperture 46 (FIG. 2). The lid 48 may be coupled to the cap 40 with a hinge such as a living hinge or other suitable fastener. The aperture 46 has a diameter that is big enough to receive a syringe needle 6 as well as the syringe nose 7 itself. The viscous liquid is prevented from drying out when the lid 48 is in the closed configuration. At least one of the cap 40 and lid 48 define a respective recess 50, 52 configured to receive a user's finger or thumb whereby to urge the lid 48 to the open configuration. The cap aperture 46 must at least be configured to receive a nose 7 of a syringe reservoir 5 far enough into the cap and base member interior areas to make contact with the liquid retention member 30. In other words, the syringe nose 7 must touch the liquid retention member 30 so that viscous liquid is left on the nose 7.

A first divider 32 is positioned in the interior area of the cap 40 between the cap aperture 46 and the liquid retention member 30. Preferably, the first divider 32 is constructed of a semi-porous material that enables a syringe needle to pierce through but does not allow the viscous liquid to pass therethrough. To this end, the first divider 32 may be constructed of a rubber or vinyl material. Similarly, a divider 34 is positioned in the interior area of the base member 20 adjacent the open bottom. Preferably, the second divider 34 is constructed of a semi-porous material that enables a syringe needle 6 to pierce through but does not allow the viscous liquid to pass therethrough. The liquid retention member 30 is essentially sandwiched between the first 32 and second 34 dividers so as to keep the viscous liquid from leaking from the base member 20 and cap 40.

Figure 3B:
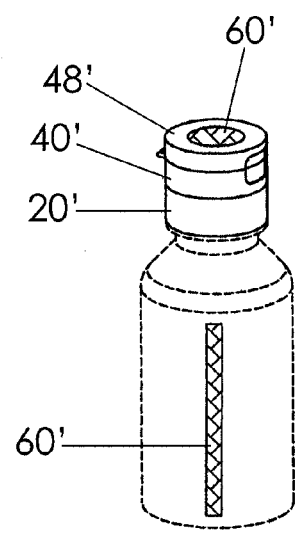
FIG. 3b is a perspective view of the marking apparatus shown coupled to a different medicine vial.

The present invention may be applicable to use of a single medicine vial as well as for use with multiple different medicine vials. For instance, a user may be required to inject himself with different types of insulin each day, each type being dispensed from a different vial. Accordingly, the injection site apparatus 10 may include multiple forms of indicia to aid in keeping multiple vials organized. The apparatus 10 for use with multiple vials is shown in FIGS. 3a and 3b.

More particularly, the apparatus may include a first indicia 60 positioned on the cap 40 of a medicine vial 2. The first indicia 60 may be one of a color, an alphanumeric symbol, a pattern, or other symbol. Further, the first indicia 60 may be applied to a top surface of the lid 48 of the cap 40, such as by being an adhesive tab or sticker. The first indicia 60 may be affixed to a cap lid 48 at a point of manufacture or applied by a user. The first indicia 60 is representative of a color of viscous liquid that is retained by the liquid retention member 30 inside the cap 40.

The apparatus 10 may also include a second indicia 62 configured to be applied to a vial 2, such as with an adhesive such as a sticker. The second indicia 62 may also be one of a color, an alphanumeric symbol, a pattern, or other symbol.

Importantly, the second indicia 62 corresponds with the first indicia 60 (e.g. same color) so that they may be matched and used together. Again, the second indicia 62 may be affixed to a medicine vial at a point of manufacture or applied by a user after receiving a supply of the vials and site marking apparatuses. For example, a marking apparatus 10 having a red first indicia 60 is to be used with a vial having a red second indicia 62 whereas a marking apparatus 10 having a blue first indicia is to be used with a vial having a blue second indicia. Therefore, it can be seen that multiple site marking apparatuses 10 may be used with multiple serum vials 2 without confusion by matching associated/corresponding first 60 and second 62 indicia members. A cap 40 having indicia of one color should be used with a vial 2 having a second indicia 62 of the same or corresponding color. In FIG. 3b, reference numerals for another/auxiliary marking apparatus, vial, and auxiliary first and second indicia are referred to with primed reference numerals, In a method of using the site marking apparatus 10, the base member 20 of a marking apparatus 10 having a first indicia 60 of a first color (or symbol or pattern) may be coupled to a vial 2 having a second indicia 62 of a corresponding color (or symbol or pattern). In cases where multiple medicines need to be injected, the base member 20 of a marking apparatus 10 having a first indicia of another color may be coupled to a vial 2 having a second indicia of said another color. Then, the needle 6 of a first syringe 4 may be inserted through the cap aperture 46 into the vial 2 so as to draw serum therefrom into the syringe reservoir 5. In doing so, the syringe reservoir nose 7 will contact the viscous liquid and be colored thereby. Next, the user may inject himself with the filled syringe 4 by inserting the needle 6 into his fatty tissue—such as leg, stomach, buttocks, or the like—until the colored nose 7 contacts the user's skin, leaving a color indication of which medicine was injected. This process may be repeated using a marking apparatus and vial having respective indicia of another color. In this way, a user knows for certain which medicine has been injected and which has not.

Accordingly, the present invention brings increased certainty to a user who injects more than a single liquid medicine on a daily or other cyclical basis.

It is understood that while certain forms of this invention have been illustrated and described, it is not limited thereto except insofar as such limitations are included in the following claims and allowable functional equivalents thereof.

The invention claimed is:

1. A method of marking a site on a person's skin that has been injected with serum taken from a serum vial with a syringe having a needle and a syringe reservoir nose so that a user does not mistakenly inject a serum more than once, said method comprising the steps of:
    providing a marking apparatus including:
        a base member defining an interior area configured to be removably coupled to the serum vial adjacent a serum vial seal;
        a liquid retention member positioned in said base member interior area that is saturated with a colorized viscous liquid;
    coupling the base member to the vial adjacent the vial seal;
    inserting the syringe needle through said liquid retention member and through the serum vial seal such that serum is selectively drawn into the syringe reservoir and that the syringe reservoir nose contacts said viscous liquid of said liquid retention member; and
    injecting the syringe needle into the user's skin until the syringe reservoir nose contacts the user's skin so as to mark the user's skin with said viscous liquid.

2. The method of marking as in claim 1, wherein said marking apparatus includes:

provinding a cap having a continuous side wall that defines an open bottom and having a top wall that defines an aperture, said cap side wall and said base member side wall having complementary cylindrical configurations and are coupled together in a friction fit engagement; and wherein said cap aperture is configured to receive said syringe needle and said syringe reservoir nose into said base interior area and into contact with said liquid retention member.

3. The method of marking as in claim 1, wherein said base member includes a bottom wall defining said open bottom, said open bottom having a diameter configured to be selectively coupled to the serum vial in a friction fit arrangement.

4. The method of marking as in claim 2, wherein said cap includes a lid selectively movable between a closed configuration preventing access to said aperture and an open configuration providing access to said aperture.

5. The method of marking as in claim 2, further comprising:

providing a first divider positioned in said interior area of said cap between said cap aperture and said liquid retention member, said first divider having a porous configuration that enables the syringe needle to pass therethrough and that prevents said viscous liquid from passing therethrough; and providing a second divider in said interior area of said base member between said base member open top and said liquid retention member, said second divider having a porous configuration that enables the syringe needle to pass therethrough and that prevents said viscous liquid from passing therethrough.

6. The method of marking as in claim 1, wherein said viscous liquid is a saline solution having a natural colorant.

7. The method of marking as in claim 2, wherein said apparatus includes:

a first indicia on said cap indicative of a color of said viscous liquid;

a second indicia configured to be applied to the serum vial, said second indicia corresponding with said first indicia so as to confirm said base member is properly coupled to the serum vial.

8. The method of marking as in claim 7, wherein:

said first indicia is attached to said cap with an adhesive; a said second indicia is attached to the serum vial with an adhesive;

said first indicia is one of a color, an alphanumeric symbol, or a pattern; and said second indicia is one of a color, an alphanumeric symbol, or a pattern.

* * * * *